United States Patent [19]

Wert et al.

[11] Patent Number: 4,540,819
[45] Date of Patent: Sep. 10, 1985

[54] PROCESS FOR PREPARING SECONDARY AMINES

[75] Inventors: Kathleen L. Wert, Philadelphia; Alan W. Tremper, Lansdowne, both of Pa.

[73] Assignee: SmithKline Beckman Corporation, Philadelphia, Pa.

[21] Appl. No.: 489,654

[22] Filed: Apr. 28, 1983

[51] Int. Cl.$^3$ .................. C07C 149/24; C07C 149/42
[52] U.S. Cl. .................................... 564/340; 564/356; 564/365
[58] Field of Search ............................... 564/340, 356

[56] References Cited

U.S. PATENT DOCUMENTS 3,345,416  10/1967  Russell et al. .................. 260/590
4,197,297   4/1980  Weinstock ........................ 424/244

OTHER PUBLICATIONS

H. Becker et al., J. Am. Chem. Soc., 85 3410, (1963).

Primary Examiner—Robert V. Hines
Attorney, Agent, or Firm—William H. Edgerton; Richard D. Foggio; Alan D. Lourie

[57] ABSTRACT

New intermediates and processes for preparing 6-halo-7,8-dihydroxy-1-(p-hydroxyphenyl)-2,3,4,5-tetrahydro-1H-3-benzazepines involve the reaction of a p-methoxyphenylglyoxal, lower alkyl hemimercaptal with a 2-chloro-3,4-dimethoxyphenethylamine, followed by a borohydride reduction.

8 Claims, No Drawings

PROCESS FOR PREPARING SECONDARY AMINES

This invention relates to a new chemical process for preparing secondary amines. More particularly, this process is for preparing N-(2-hydroxy-2-phenylethyl)-2-phenethylamines, for example, N-[2-hydroxy-2-(p-methoxyphenyl)ethyl]-2-(2-halo-3,4-dimethoxyphenyl)ethylamines. The latter are chemical intermediates for preparing 6-halo-7,8-dihydroxy-1-(p-hydroxyphenyl)-2,3,4,5-tetrahydro-1H-3-benzazepines which are dopaminergic agents useful for treating hypertension or kidney dysfunction.

BACKGROUND OF THE INVENTION

U.S. Pat. No. 4,197,297, issued Apr. 8, 1980, describes two processes for preparing N-[2-hydroxy-2-(p-methoxyphenyl)ethyl]-2-(2-chloro-3,4-dimethoxyphenyl)ethylamine. The first involves reaction of 2-chloro-3,4-dimethoxyphenethylamine with p-methoxystyrene oxide and the second, condensation of 2-bromo-1-t-butoxy-1-(p-methoxyphenyl)ethane with 2-chloro-3,4-dimethoxyphenethylamine followed by removal of the t-butyl protective group. The intermediates and process of this invention are not only chemically unobvious from the previous art but give better yields with lower chemical and through-put costs.

The starting materials for the process of this invention are p-methoxyphenylglyoxal lower alkyl hemimercaptals which are described in U.S. Pat. No. 3,345,416 and H. Becker, et al., J. Am. Chem. Soc., 85 3410 (1963). These publications do not describe the facile reaction of the hemimercaptals with primary amines.

DESCRIPTION OF THE INVENTION

The process of this invention is illustrated by the following reaction sequence:

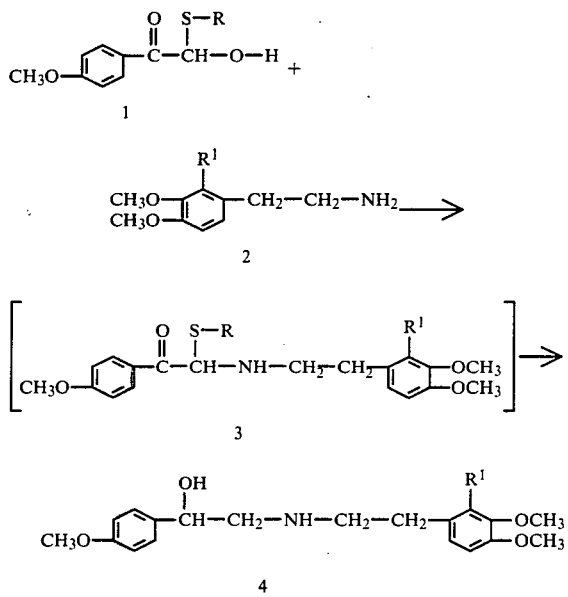

in which R is lower alkyl of 1-4 carbons, preferably methyl, and $R^1$ is chloro or fluoro.

One skilled in the art will recognize that substituents on the respective phenyl rings of the two starting materials will not, to the best of our knowledge, influence the chemical reaction of the hemimercaptal of formula 1 with the phenethylamine of formula 2. For example, the methoxy substituents may be replaced by hydrogen, higher alkoxy groups, ethylenedioxy or methylenedioxy, the latter two on the methoxy substituted phenethylamine. The 2-halo substituent may also be replaced by hydrogen, trifluoromethyl, lower alkyl, lower alkylthio or similar substituents as known to the benzazepine art.

The chemical process of this invention comprises the reaction of the hemimercaptal of formula 1 and the phenethylamine of formula 2 in an organic solvent, which is inert to the reactants and in which the reactants are substantially soluble, until the coupling is complete. An excess of either starting material may be optionally present but usually stoichiometric quantities are used. In fact, an excess of the primary amine may give better yields of isolated thioether intermediate of formula 3. Suitable solvents are selected from the preferred lower alcohols such as methanol, ethanol, propanol or isopropanol, ethers such as tetrahydrofuran, dimethylsulfoxide, dimethylformamide, dimethyl acetamide, aromatics such as benzene, toluene or xylene, esters such as ethyl acetate, halohydrocarbons such as chloroform, carbon tetrachloride, ethylene dichloride, methylene chloride or mixtures thereof. Methanol or aqueous mixtures of methanol are preferred.

The reaction is conveniently run at room temperature until complete, usually from 1–12 hours. If the phenethylamine is used in the form of an acid addition salt, such as the hydrochloride or hydrobromide, an equivalent quantity of an acid binding agent, such as an alkali metal lower alkoxide, hydroxide or carbonate, is added to generate the base in situ.

Higher temperatures, up to the reflux temperature, of the reaction mixture, are optionally used, such as when the solubility of a starting material is a problem. When methanol is used as solvent, the intermediate of formula 3, for example, N-[2-(2-chloro-3,4-dimethoxyphenyl)ethyl]-2-keto-2-(p-methoxyphenyl)-1-methyl-thioethylamine, is easily separated from the reaction mixture by precipitation. The thioether intermediates of formula 3 are new compounds and are an important aspect of this invention.

Optionally, the operator may isolate the α-thio intermediate of formula 3 or he may continue with the reactions of Sequence A without isolation. The α-thio compound is treated with a reducing agent capable of converting a keto group to a hydroxy group. Unexpectedly, this reaction simultaneously removes the α-alkylthio group in the form of a lower alkyl mercaptan by-product. Reducing agents include the traditional ones which are used in the art to convert a keto group to a hydroxy. Examples are metal-acid, such as zinc dust-acetic acid or iron and acetic acid, zinc-sodium hydroxide in ethanol or a Meerwein reduction. Splitting a ring methoxy substituent during the reduction is not unacceptable but care should be taken to use a reducing agent which will not attack halo substituents.

More suitable reduction means, especially when a halo is present on one of the phenyl rings of compound 3, are the borohydride reducing agents. Most useful of these are the alkali metal borohydrides, such as sodium or potassium borohydride. Others include; the alkali metal trialkylborohydrides, such as lithium or potassium trisiamylborohydrides and lithium or potassium tri-sec.-butylborohydrides, the alkali metal trialkoxyborohydrides such as sodium or potassium triisopropoxyborohydrides. Also useful are the corresponding hydrides such as lithium aluminum hydride, sodium aluminum hydride, diisobutyl aluminum hydride, sodium diethylaluminum hydride or sodium bis-(2-methoxyethoxy)aluminum hydride.

Organic solvents commonly used in hydride or borohydride reactions will be recognized as applicable to this reaction, for example, lower alcohol, tetrahydrofuran, glyme, diglyme, dimethylformamide, sulfolane.

Most usefully, the reaction is carried out using at least two equivalents of sodium borohydride in methanol until the reaction is complete, maintaining the temperature below 20° initially, then, allowing it to obtain room temperature. The overall yield of the one-pot, two step reaction runs from 50–80% of product which is isolated by standard chemical procedures. If the overall two step reaction of Sequence A is run without isolation of the thioether, the solvent must be selected to accommodate the reducing agent.

The secondary amines of formula 4 are converted into biologically active end products as described in Example 2 of U.S. Pat. No. 4,197,297. For example, the secondary amine is treated with concentrated sulfuric acid-trifluoroacetic acid or methanesulfonic acid-methylene chloride to form the benzazepine ring. Protective groups such as alkyl ethers, if present, are, then, split using boron tribromide-methylene chloride or 48% hydrobromic acid to obtain the desired end product.

The following examples are designed to illustrate the practice of this invention. All temperatures are Centigrade. Other variations of these examples will be obvious to those skilled in the art.

EXAMPLE 1

A 22 L flask was charged with 526.6 g (2.48 m) of p-methoxyphenylglyoxal methyl hemimercaptal and 626.3 g (2.48 m) of 2-chloro-3,4-dimethoxyphenethylamine hydrochloride followed by 7.4 L of methanol and 535.8 g (2.48 m) of 25% sodium methoxide/methanol. The mixture was stirred at room temperature for 3 hours, then, chilled to 0°. Sodium borohydride (200 g, 5.26 m) was added at a rate which maintained reaction temperature below 20°. The mixture was stirred for 8 hours while allowing the reaction mixture to warm to room temperature. The methanol was stripped off in vacuo at less than 50°. About 2.5 L of 10% hydrochloric acid was added to give a pH of 1. Methylene chloride (2.25 L) was added. The mother organic extract combined with two follow-up liter extracts was taken to half volume at which time 5.6 L of ethyl acetate was added. After stirring until the desired product had separated completely, 505.19 g (50.8%) of N-[2-hydroxy-2-(p-methoxyphenyl)ethyl]-2-(2-chloro-3,4-dimethoxyphenyl)ethylamine was recovered by filtration, washing with 1 L of ethyl acetate and oven drying. This material was identical with that described in the prior art by NMR.

EXAMPLE 2

A. A mixture of 3.6 g (0.017 m) of p-methoxyphenyl-glyoxal methyl hemimercaptal, 4.61 g (0.0213 m) of 2-chloro-3,4-dimethoxyphenethylamine and 70 ml of methanol was stirred at room temperature for 3 hours. The precipitated solid was separated by filtration, washed with propanol and air-dried to give 5.53 g (79%) of N-[2-(2-chloro-3,4-dimethoxyphenyl)ethyl]-2-keto-2-(p-methoxyphenyl)-1-methylthioethylamine, m.p. 75°–78°.

Anal. Calcd. for $C_{20}H_{24}NSO_4Cl$: C, 58.60; H, 5.90; N, 3.42; S, 7.82; Cl, 8.65. Found: C, 58.47; H, 5.98; N, 3.43; S, 8.01; Cl, 9.00.

B. A mixture of 3.40 g (16 mm) of p-methoxyphenyl-glyoxal methyl hemimercaptal, 3.46 (16 mm) of 2-chloro-3,4-dimethoxyphenethylamine and 90 ml of methanol was stirred at room temperature for 72 hours. Methanol was stripped off to give an oil. Methanol (20 ml) was added with no crystallization upon chilling. Two ml of cyclohexane was added. With chilling, 1.86 g of the thioether separated.

A portion of the thioether (0.3 g, 0.73 mm) in methanol was reacted with 0.06 g (1.46 mm) of sodium borohydride. After 1 hour, all the reactants had gone into solution. High pressure, liquid chromatographic reverse phase analysis (HPLC), (over silica with 60:40 methanol/water buffered with acetic acid and octanesulfonic acid as mobile phase) demonstrated almost quantitative conversion to N-[2-hydroxy-2-(p-methoxyphenyl)ethyl]-2-(2-chloro-3,4-dimethoxyphenyl)ethylamine.

The methylthio compound (500 mg) dissolved in an acid solution (HPLC acid phase from above) at pH 3 was allowed to stand for 24 hours, at which time, there was demonstrated disappearance of the methylthio absorption at 10 min. and appearance of peaks corresponding to hemimercaptal (34%) and primary amine (9%).

EXAMPLE 3

A mixture of 3.9 g (2 mm) of 2-fluoro-3,4-dimethoxyphenethylamine, 4.4 g (2 mm) of p-methoxyglyoxal methyl hemimercaptal and 10 ml of ethanol is reacted at 35° for two hours. Brief concentration and cooling gives N-[2-(2-fluoro-3,4-dimethoxyphenyl)-ethyl]-2-keto-2-(p-methoxyphenyl)-1-methylthioethylamine.

The methylthio intermediate (1.5 g) is reacted with two equivalents of sodium borohydride in tetrahydrofuran at 40° to give N-(2-hydroxy-2-(p-methoxyphenyl)ethyl]-2-(2-fluoro-3,4-dimethoxyphenyl)ethylamine.

What is claimed is:

1. A process for preparing a compound of the formula:

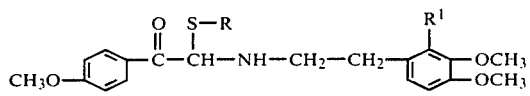

in which:

R is lower alkyl of 1–4 carbons, and $R^1$ is chloro or fluoro, comprising the step of reacting a compound of the formula:

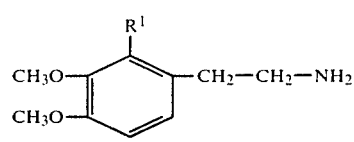

in which $R^1$ is as defined above, with a compound of the formula:

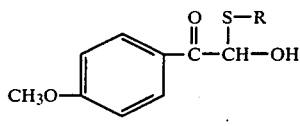

in which R is as defined above, in an organic solvent which is chemically inert to the reactants and in which the reactants are substantially soluble.

2. The process of claim 1 in which R is methyl and $R^1$ is chloro.

3. The process of claim 1 in which R is methyl and $R^1$ is fluoro.

4. The process of claim 1 in which the solvent is methanol or aqueous methanol.

5. A process for preparing a compound of the formula:

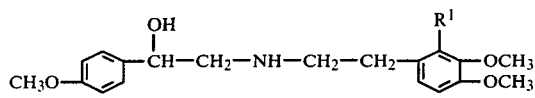

in which $R^1$ is chloro or fluoro, comprising the steps of reacting a compound of the formula:

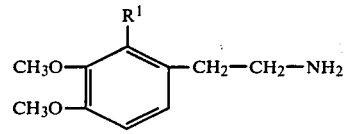

in which $R^1$ is as defined above with a p-methoxyphenylglyoxal lower alkyl hemimercaptal to prepare a thio compound of the formula:

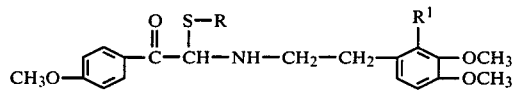

in which R is lower alkyl and $R^1$ is as defined above, and reacting said thio compound with a borohydride reducing agent.

6. The process of claim 5 in which R is methyl and the borohydride reducing agent is sodium borohydride.

7. The process of claim 6 in which the reactions are carried out in methanol.

8. The process of claim 7 in which the two steps are run without isolation of the thioether intermediate.

* * * * *